United States Patent
Liao et al.

(10) Patent No.: US 10,509,008 B2
(45) Date of Patent: Dec. 17, 2019

(54) BIOLOGICAL DEVICE AND BIOSENSING METHOD THEREOF

(71) Applicant: TAIWAN SEMICONDUCTOR MANUFACTURING CO., LTD., Hsinchu (TW)

(72) Inventors: Ta-Chuan Liao, Taichung (TW); Chien-Kuo Yang, Taipei (TW); Yi-Shao Liu, Zhubei (TW); Tung-Tsun Chen, Hsinchu (TW); Chan-Ching Lin, Hsinchu (TW); Jui-Cheng Huang, Hsinchu (TW); Felix Ying-Kit Tsui, Cupertino, CA (US); Jing-Hwang Yang, Zhubei (TW)

(73) Assignee: Taiwan Semiconductor Manufacturing Co., Ltd. (TW)

(*) Notice: Subject to any disclaimer, the term of this patent is extended or adjusted under 35 U.S.C. 154(b) by 206 days.

(21) Appl. No.: 14/700,133

(22) Filed: Apr. 29, 2015

(65) Prior Publication Data
US 2016/0320335 A1    Nov. 3, 2016

(51) Int. Cl.
*G01N 27/414* (2006.01)

(52) U.S. Cl.
CPC .................. *G01N 27/4145* (2013.01)

(58) Field of Classification Search
CPC .......................................... G01N 27/414–4148
See application file for complete search history.

(56) References Cited

U.S. PATENT DOCUMENTS

| 4,180,771 | A | * | 12/1979 | Guckel | ............ | A61B 5/14542 |
|           |   |   |         |        |              | 204/418 |
| 5,702,981 | A |   | 12/1997 | Maniar et al. |||
| 6,628,982 | B1 |  | 9/2003 | Thomas et al. |||
| 7,060,510 | B2 |  | 6/2006 | Bonnell et al. |||
| 7,306,924 | B2 |  | 12/2007 | Gomez et al. |||
| 7,632,670 | B2 |  | 12/2009 | Offenhausser et al. |||
| 7,695,609 | B2 |  | 4/2010 | Soundarrajan et al. |||
| 7,696,530 | B2 |  | 4/2010 | Yamamoto et al. |||

(Continued)

FOREIGN PATENT DOCUMENTS

| CN | 101728276 A | 6/2010 |
| CN | 101764091 A | 6/2010 |

(Continued)

OTHER PUBLICATIONS

Yin, Li-Te, et al. "Characteristics of silicon nitride after O/sub 2/plasma surface treatment for pH-ISFET applications." IEEE transactions on biomedical engineering 48.3 (2001): 340-344.*

(Continued)

*Primary Examiner* — Robert J Eom
(74) *Attorney, Agent, or Firm* — Sterne, Kessler, Goldstein & Fox P.L.L.C.

(57) ABSTRACT

A biological device includes a substrate, a gate electrode, and a sensing well. The substrate includes a source region, a drain region, a channel region, a body region, and a sensing region. The channel region is disposed between the source region and the drain region. The sensing region is at least disposed between the channel region and the body region. The gate electrode is at least disposed on or above the channel region of the substrate. The sensing well is at least disposed adjacent to the sensing region.

26 Claims, 8 Drawing Sheets

(56) References Cited

U.S. PATENT DOCUMENTS

| | | | |
|---|---|---|---|
| 7,833,708 | B2 | 11/2010 | Enzelberger et al. |
| 7,923,314 | B2 | 4/2011 | Tezuka et al. |
| 8,007,727 | B2 | 8/2011 | Shalev et al. |
| 8,420,328 | B2 | 4/2013 | Chen et al. |
| 8,471,559 | B2 | 6/2013 | Taherian et al. |
| 8,519,490 | B2 | 8/2013 | Bikumandla |
| 8,557,643 | B2 | 10/2013 | Han et al. |
| 8,728,844 | B1 | 5/2014 | Liu et al. |
| 8,729,546 | B2 | 5/2014 | Suzawa et al. |
| 8,778,269 | B2 | 7/2014 | Joshi et al. |
| 8,871,549 | B2 | 10/2014 | Ellis-Monaghan et al. |
| 8,878,258 | B2 | 11/2014 | Monfray et al. |
| 9,080,969 | B2 | 7/2015 | Liu et al. |
| 9,184,189 | B2 | 11/2015 | Uochi et al. |
| 9,219,158 | B2 | 12/2015 | Miyairi et al. |
| 9,389,199 | B2 | 7/2016 | Cheng et al. |
| 9,417,209 | B2 | 8/2016 | Shen et al. |
| 9,419,113 | B2 | 8/2016 | Asano et al. |
| 9,459,234 | B2 | 10/2016 | Kalnitsky et al. |
| 9,601,601 | B2 | 3/2017 | Sakata |
| 9,704,976 | B2 | 7/2017 | Asano et al. |
| 9,768,280 | B2 | 9/2017 | Yamazaki |
| 2005/0156207 | A1* | 7/2005 | Yazawa ............... G01N 27/414 257/288 |
| 2007/0155005 | A1 | 7/2007 | Valerio et al. |
| 2013/0105868 | A1 | 5/2013 | Kalnitsky et al. |
| 2013/0200438 | A1* | 8/2013 | Liu ..................... G01N 27/414 257/253 |
| 2014/0264468 | A1 | 9/2014 | Cheng et al. |

FOREIGN PATENT DOCUMENTS

| | | |
|---|---|---|
| CN | 101847631 A | 9/2010 |
| CN | 101859799 A | 10/2010 |
| CN | 101901838 A | 12/2010 |
| CN | 102257621 A | 11/2011 |
| CN | 103091368 A | 5/2013 |
| CN | 104049021 A | 9/2014 |
| CN | 104078512 A | 10/2014 |
| CN | 104212711 A | 12/2014 |
| KR | 101287445 B1 | 7/2013 |
| TW | 200902130 A | 1/2009 |

OTHER PUBLICATIONS

Ito, T. A. D. A. S. H. I., H. A. Z. I. M E. Inagaki, and I. Igarashi. "ISFET's with ion-sensitive membranes fabricated by ion implantation." IEEE Transactions on Electron Devices 35.1 (1988): 56-64.*
"Lateral." Merriam-Webster.com. Merriam-Webster, n. d. Web. Sep. 14, 2017.*
Kim, Dong-Sun, et al. "An extended gate FET-based biosensor integrated with a Si microfluidic channel for detection of protein complexes." Sensors and Actuators B: Chemical 117.2 (2006): 488-494.*
Jonghyun Go et al., (2010) Beating the Nernst limit of 59mV/pH with Double-Gated Nano-Scale Field-Effect Transistors and Its Applications to Ultra-Sensitive DNA Biosensors. IEEE.
Shinwari et al., "Study of the electrolyte-insulator-semiconductor field-effect transistor (EISFET) with applications in biosensor design", Microelectronics Reliability, vol. 47, Issue 12, pp. 2025-2057.

* cited by examiner

BIOLOGICAL DEVICE AND BIOSENSING METHOD THEREOF

BACKGROUND

Biosensors are devices for sensing and detecting biomolecules. The biosensors operate on the basis of electronic, electrochemical, optical, or mechanical detection principles. Biosensors including transistors are sensors that electrically sense charges, photons, or mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A biological device and the method of bio-sensing are provided in accordance with various exemplary embodiments. The variations of the embodiments are discussed. Throughout the various views and illustrative embodiments, like reference numbers are used to designate like elements.

Figure 1A:
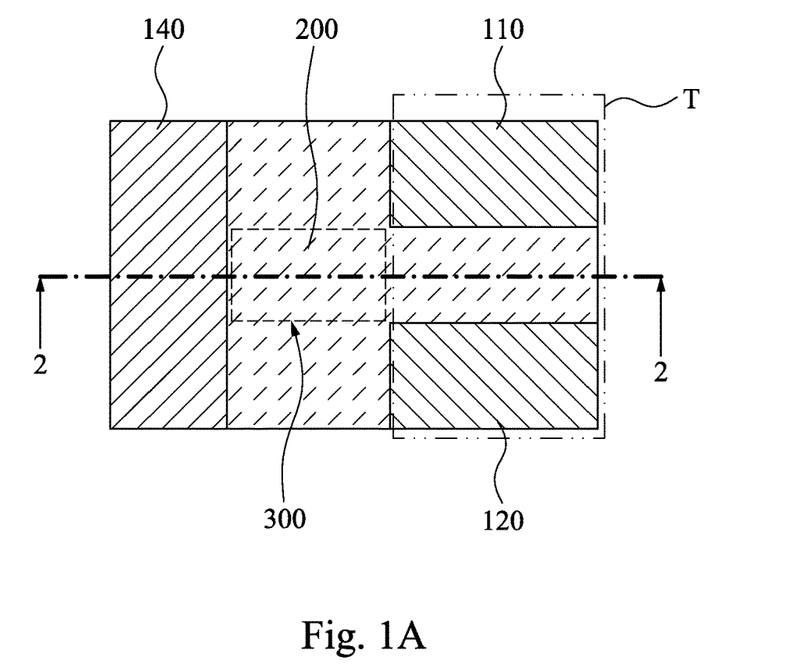
FIG. 1A is a top view of a biological device in accordance with some embodiments.
Figure 1B:
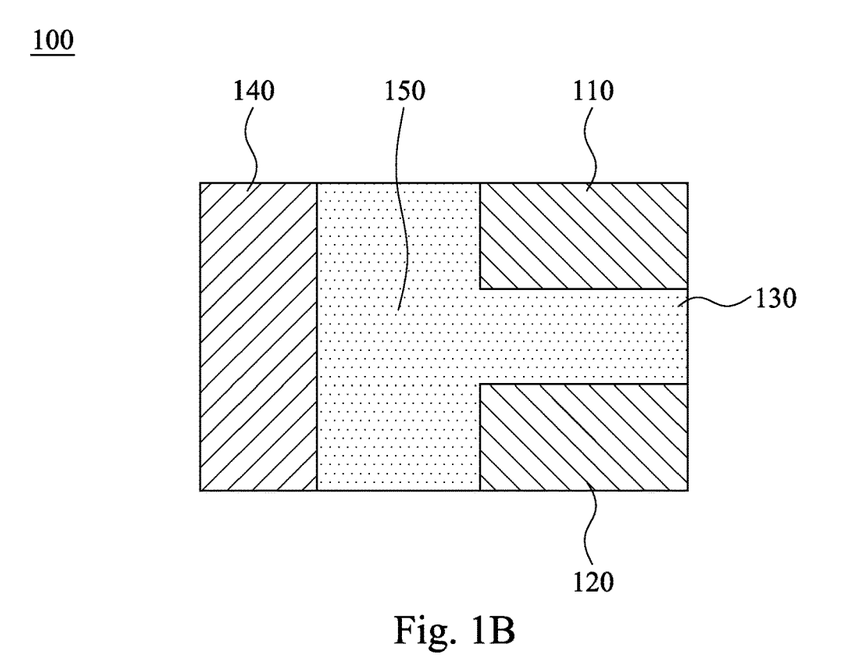
FIG. 1B is a top view of a substrate of the biological device of FIG. 1A.
Figure 2:
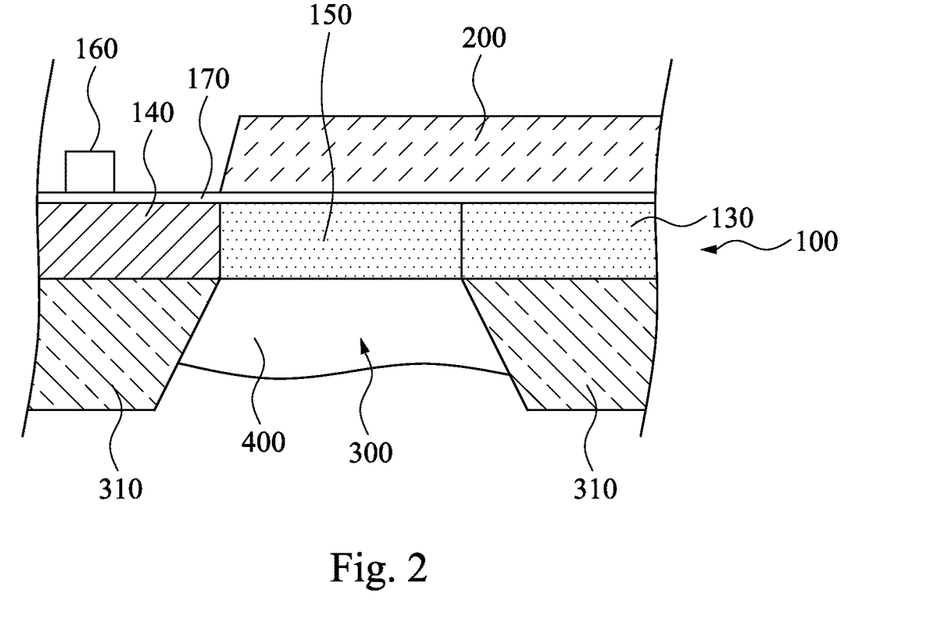
FIG. 2 is a cross-sectional view taking along line 2-2 of FIG. 1A.

FIG. 1A is a schematic diagram of a biological device in accordance with some embodiments, FIG. 1B is a top view of a substrate 100 of the biological device of FIG. 1A, and FIG. 2 is a cross-sectional view taking along line 2-2 of FIG. 1A. For clarity, the gate dielectric 170 is depicted in FIG. 2 and is omitted in FIGS. 1A and 1B. As shown in FIGS. 1A to 2, the biological device includes a substrate 100, a gate electrode 200, and a sensing well 300. The substrate 100 includes a source region 110, a drain region 120, a channel region 130, a body region 140, and a sensing region 150. The channel region 130 is disposed between the source region 110 and the drain region 120. The sensing region 150 is at least disposed between the channel region 130 and the body region 140. The gate electrode 200 is at least disposed on or above the channel region 130 of the substrate 100. The sensing well 300 is at least disposed adjacent to the sensing region 150. In other words, the sensing well 300 exposes the sensing region 150 of the substrate 100, and the sensing well 300 is aligned with the sensing region 150. The sensing well 300 is the region used to detect biomolecules.

From another point of view, the source region 110 and the drain region 120 are respectively disposed at opposite sides of the channel region 130. The body region 140 is separated from the channel region 130. The sensing region 150 is physically connected the body region 140 to the channel region 130, and the body region 140 and the channel region 130 are respectively disposed at opposite sides of the sensing region 150. The gate electrode 200 is at least disposed on or above the channel region 130.

In FIGS. 1A to 2, the gate electrode 200 is further disposed on the sensing region 150, and the sensing well 300 is disposed beneath the sensing region 150. In other words, the sensing region 150 is disposed between the gate electrode 200 and the sensing well 300, and the gate electrode 200 and the sensing well 300 are respectively disposed at opposite sides of the sensing region 150.

Figure 3:
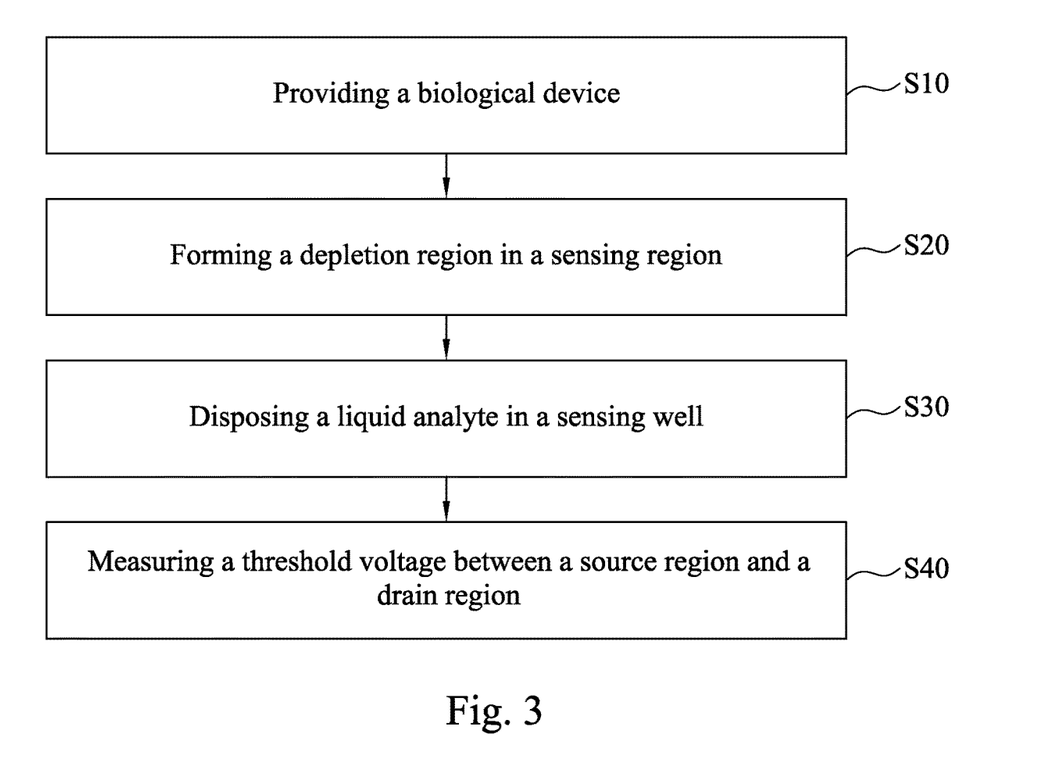
FIG. 3 is a flow chart of a method for bio-sensing in accordance with some embodiments.

The following paragraphs provide detailed explanations with respect to how to use a biological device to sense biomolecules. FIG. 3 is a flow chart of a method for bio-sensing in accordance with some embodiments. To describe clarified, the method can be applied to, but should not be limited to, the biological device of FIG. 1A. As shown in operation S10, a biological device is provided. In some embodiments, the biological device of FIG. 1A is provided.

Subsequently, as shown in operation S20, forming a depletion region in the sensing region 150, such that at least partial of the sensing region 150 is depleted. In other words, at least partial of the sensing region 150 is the depletion region. The "depletion region" herein is an insulating region within a conductive and doped semiconductor material where the mobile charge carriers have been forced away, or have diffused away by an electric field. Hence, the elements left in the depletion region are ionized donor or acceptor impurities.

In some embodiments, a plasma treatment is performed to the sensing region 150 to make the sensing region 150 become depleted. In some other embodiments, an ion implantation process is performed to the sensing region 150 to make the sensing region 150 become depleted. The plasma treatment and the ion implantation process can be done during the biological device is manufactured, and the claimed scope of the present disclosure is not limited in this respect.

In still some other embodiments, a bias is applied to the body region 140 to make the sensing region 150 become depleted. For example, a bias source 160 (see FIG. 2) can be electrically connected to the body region 140. The sensing region 150 can be a non-depletion region when the bias is not applied. When the bias is applied to the body region 140, an electric field is generated in the sensing region 150 and at least partial of the sensing region 150 becomes depleted.

Figure 4A:
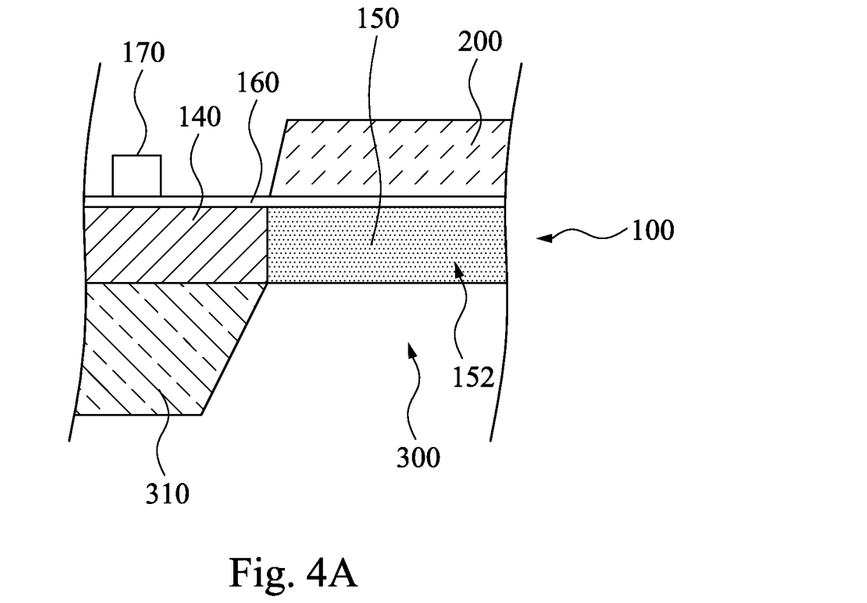
FIG. 4A is a cross-sectional view of the biological device of FIG. 2 when a bias is applied to a body region.

For example, FIG. 4A is a cross-sectional view of the biological device of FIG. 2 when the bias is applied to the body region 140. Reference is made to FIGS. 1B and 4A. In FIG. 4A, almost the entire sensing region 150 is the depletion region 152 when the bias is applied to the body region 140. Therefore, current is not allowed to flow from the body region 140 to the channel region 130. However, in some other embodiments, the depletion region 152 may occupy a portion of the sensing region 150. Basically, embodiments fall with the claimed scope if at least partial of the sensing region 150 is the depletion region 152.

Reference is made to FIGS. 1A-3. As shown in operation S30, a liquid analyte 400 is disposed in the sensing well 300. The liquid analyte 400 includes target molecules that would bind to the sensing region 150. The reaction and bound target molecules are sensed by the biological device. In some embodiments, the liquid analyte 400 includes biological molecules, such as single-stranded deoxyribonucleic acid (ssDNA) or single nucleotide polymorphism (SNP). The liquid analyte 400 is disposed in the sensing well 300. The molecules of the liquid analyte 400 may be charged biomolecules, which then move close to the sensing region 150 and change the electrical performance thereof.

Figure 4B:
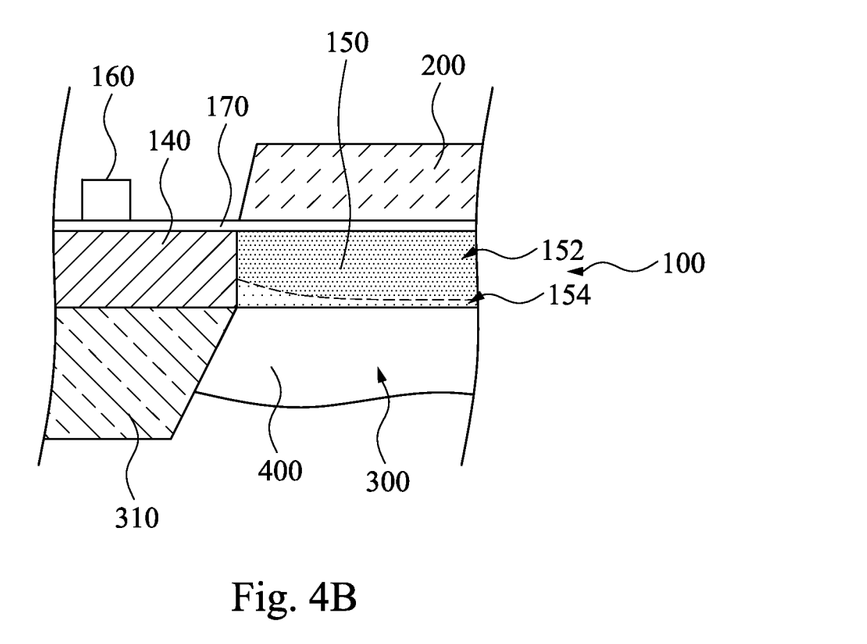
FIG. 4B is a cross-sectional view of the biological device of FIG. 2 when a liquid analyte is disposed in a sensing well.

For example, FIG. 4B is a cross-sectional view of the biological device of FIG. 2 when the liquid analyte 400 is disposed in the sensing well 300. The charged biomolecules may change the electric field of the sensing region 150, and therefore, the depletion behavior of the depletion region 152 is changed accordingly. In FIG. 4B, for example, the depletion region 152 is reduced and a channel 154 is formed in the sensing region 150. Hence, current can flow from the body region 140 to the channel region 130.

It is noted that the depletion behavior of the depletion region 152 changed in the sensing region 150 in FIGS. 4A and 4B are illustrative, and should not limit the claimed scope of the present disclosure. In some other embodiments, a channel can be formed in the sensing region 150 when the liquid analyte 400 is absent, and the channel is blocked when the liquid analyte 400 is disposed (or filled) in the sensing well 300. Basically, embodiments fall within the claimed scope of the present disclosure if the depletion behavior of the depletion region 152 is changed when the liquid analyte 400 is disposed in the sensing well 300.

Reference is made to FIGS. 1A-3. As shown in operation S40, a threshold voltage between the source region 110 and the drain region 120 is measured. Specifically, the source region 110, the drain region 120, the channel region 130, and the gate electrode 200 can form a transistor T, and the threshold voltage of the transistor T depends on the current of the channel region 130. As mentioned above, since the liquid analyte 400 changes the depletion behavior of the depletion region 152 of the sensing region 150, the current amount flowing from the body region 140 to the channel region 130 is changed according to the charging degree of the charging biomolecules of the liquid analyte 400. Hence, the current in the channel region 130 is changed accordingly, affecting the threshold voltage of the transistor T. Therefore, the charging molecules of the liquid analyte 400 can be sensed by measuring the threshold voltage.

In FIGS. 1A-3, the liquid analyte 400 can change the depletion behavior of the depletion region 152 in the sensing region 150. Therefore, the threshold voltage of the transistor T can be changed accordingly. Since the depletion behavior of the depletion region 152 is sensitive to the charging performance of the liquid analyte 400, the sensitivity of the biological device of FIG. 1A can be improved. Furthermore, the source region 110, the drain region 120, the channel region 130, and the gate electrode 200 in FIG. 1A can form a switch (i.e., the transistor T) to control the on/off state of the biological device. While a conventional biological device uses an additional switch to control the on/off state of the biological device, the biological device in FIG. 1A does not connect to an additional switch, which occupies an additional area, resulting in a small device size. Hence, the density of the biological devices can be increased.

It is noticed that the flow chart of FIG. 3 shows exemplary operations, but they may not performed in the order shown. Operations may be added, replaced, and/or changed order as appropriate, in accordance with the spirit and scope of disclosed embodiments.

Reference is made again to FIG. 1A. The substrate 100 is a semiconductor substrate. The substrate 100 may be a silicon substrate or wafer. Alternatively, the substrate 100 may include another elementary semiconductor, such as germanium (Ge); a compound semiconductor including silicon carbide (SiC), gallium arsenic (GaAs), gallium phosphide (GaP), indium phosphide (InP), indium arsenide (InAs), and/or indium antimonide (InSb); an alloy semiconductor including SiGe, GaAsP, AlInAs, AlGaAs, GaInAs, GaInP, and/or GaInAsP; or combinations thereof. In various embodiments, the substrate 100 is a silicon-on-insulator (SOI) substrate.

The substrate 100 may be doped, such as P-type and N-type, to form the source region 110, the drain region 120, the channel region 130, the body region 140, and the sensing region 150. In some embodiments, the source region 110 and the drain region 120 are N-doped regions, and the channel region 130, the body region 140, and the sensing region 150 are P-doped regions. Hence, the transistor T is a P-channel transistor. In some other embodiments, the source region 110 and the drain region 120 are P-doped regions, and the channel region 130, the body region 140, and the sensing region 150 are N-doped regions. Hence, the transistor T is an N-channel transistor.

In FIG. 2, the biological device further includes a gate dielectric 170 disposed between the gate electrode 200 and the substrate 100. The gate dielectric 170 may be formed of silicon oxide (SiOx). In some other embodiments, the gate dielectric 170 includes silicon nitride (SiNx), silicon oxynitride (SiON), a dielectric with a high dielectric constant (high k), and/or combinations thereof. Examples of high k materials include hafnium silicate, hafnium oxide, zirconium oxide, aluminum oxide, tantalum pentoxide, hafnium dioxide-aluminum ($HfO_2$—Al2O3) alloy, or combinations thereof.

Reference is made to FIGS. 1A and 1B. The gate electrode 200, the source region 110, the drain region 120, and the channel region 130 may be formed using suitable CMOS process technology. The transistor T may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; etching including wet etching, dry etching, and plasma etching; and/or other suitable CMOS processes. In some embodiments, the gate electrode 200 is made of polysilicon. In some other embodiments, the gate electrode 200 includes metal gate electrodes including material such as, Cu, W, Ti, Ta, Cr, Pt, Ag, Au, suitable metallic compounds like TiN, TaN, NiSi, CoSi, or combinations of these conductive materials.

In FIG. 2, the sensing well 300 may be formed by a buried oxide (BOX) layer 310. In greater detail, the buried oxide layer 310 may be disposed at a side of the substrate 100 opposite to the gate electrode 200, and the opening inside the buried oxide layer 310 forms the sensing well 300. In some embodiments, the buried oxide layer 310 is silicon dioxide ($SiO_2$).

Figure 5:
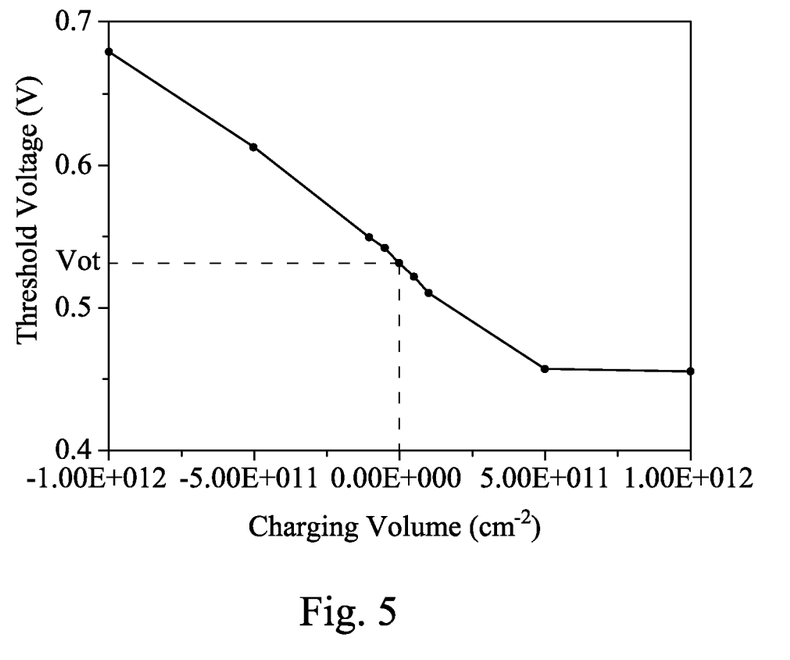
FIG. 5 is a graph of threshold voltage of the biological device of FIG. 1A as a function of the charging volume of the liquid analyte.

FIG. 5 is a graph of threshold voltage of the biological device of FIG. 1A as a function of the charging volume of the liquid analyte 400. The charging volume is the equivalent charges bonded at the sensing well 300 from the liquid analyte 400. The unit of the charging volume is $cm^{-2}$, and the unit of threshold voltage is Voltage (V). Reference is made to FIGS. 1B, 4A and 5. As mentioned above, in some embodiments, the source region 110 and the drain region 120 are N-doped regions, and the channel region 130, the body region 140, and the sensing region 150 are P-doped regions. A negative bias (such as about −2.5 V) can be applied to the body region 140 to form the depletion region 152 in the sensing region 150 (as shown in FIG. 4A). In this case, the current flowing from the body region 140 to the channel region 130 is almost blocked by the depletion region 152, and the biological device has an original threshold voltage Vot.

Reference is made to FIGS. 1B, 4B and 5. When the liquid analyte 400 having negative charging molecules is disposed in the sensing well 300, the negative charging biomolecules may be close to the sensing region 150 and change the depletion behavior of the depletion region 152. For example, the depletion behavior of the depletion region 152 is less depleted, and a channel 154 is formed in the sensing region 150 to allow the current from the body region 140 to pass therethrough. Therefore, the threshold voltage of the biological device is increased. Furthermore, as the charging volume of the negative charging molecules increases, the threshold voltage increases.

In some other embodiments, the liquid analyte 400 may have positive charging biomolecules, which causes the depletion region 152 of the sensing region 150 more depleted. Hence, the current from the body region 140 is more difficult to pass the sensing region 150, and the threshold voltage is decreased. Furthermore, as the charging volume of the positive charging biomolecules increases, the threshold voltage decreases. Therefore, by forming the depletion region 152 in the sensing region 150, the charging molecules in the liquid analyte 400 can affect the depletion behavior of the depletion region 152 and thus be sensed by the biological device.

In some embodiments, the bias source 160 is a tunable bias source, which can tune the depletion behavior of the sensing region 150 according to the sensitivity of the biological device. Furthermore, although in FIGS. 4A and 4B, the depletion region 152 is formed by applying a negative bias to the body region 140, the depletion region 152 can be formed using a plasma treatment or ion implantation process in some other embodiments. Basically, embodiments fall within the claimed scope if a depletion region 152 is formed in the sensing region 150 and the depletion behavior of the depletion region 152 is changed according to the charging volume of the liquid analyte 400.

Reference is made again to FIGS. 1B and 2. As mentioned above, in some other embodiments, the source region 110 and the drain region 120 are P-doped regions, and the channel region 130, the body region 140, and the sensing region 150 are N-doped regions. A positive bias (such as about +2.5 V) can be applied to the body region 140 to form a depletion region in the sensing region 150. In this case, the biological device has another original threshold voltage.

When the liquid analyte 400 is disposed in the sensing well 300, the depletion behavior of the depletion region is changed. In some embodiments, as the charging volume of the negative charging biomolecules increases, the threshold voltage decreases, and as the charging volume of the positive charging biomolecules increases, the threshold voltage increases. Also, the depletion region can be formed using a plasma treatment or ion implantation process in some other embodiments.

Reference is made to FIGS. 1A to 2. In the aforementioned embodiments, a depletion region can be formed in the sensing region 140 of the substrate 100. When the liquid analyte 400 is disposed in the sensing well 300, the charging biomolecules therein can affect the depletion behavior of the depletion region, thereby affecting the threshold voltage of the transistor T. Furthermore, the threshold voltage is changed according to the charging volume and the charge type (positive or negative charged) of the charging biomolecules. Hence, by measuring the threshold voltage, the charging volume and the charge type of the charging biomolecules can be identified.

In FIG. 1B, the sensing region 150 is further disposed between the source region 110 and the body region 150 and between the drain region 110 and the body region 150. In other words, the source region 110 and the body region 150 are respectively disposed at opposite sides of the sensing region 150, and the drain region 120 and the body region 150 are respectively disposed at opposite sides of the sensing region 150. Therefore, the sensing region 150 and the channel region 130 form a T-shaped figure. The sensing well 300 is disposed beneath a portion of the sensing region 150 disposed between the channel region 130 and the body region 140. However, the size and the position of the sensing well 300 is not limited in this respect.

Figure 6A:
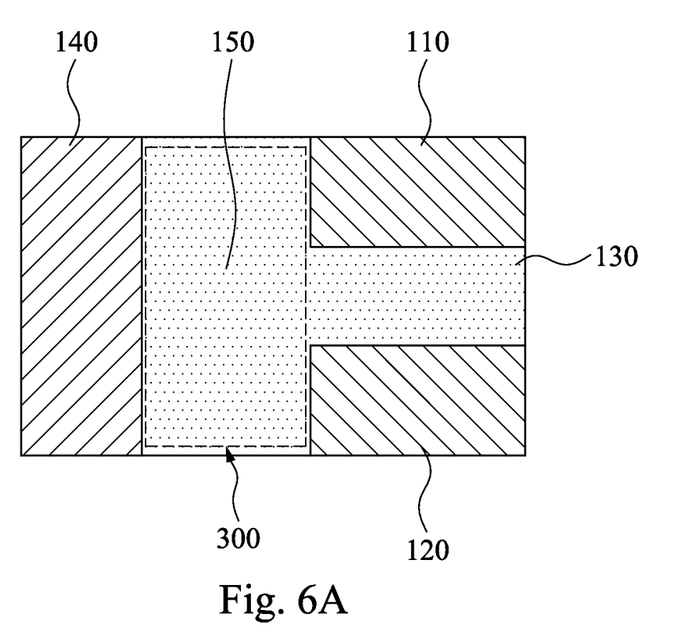
FIGS. 6A-6C are top views of substrates and sensing wells in accordance with some embodiments.
Figure 6B:
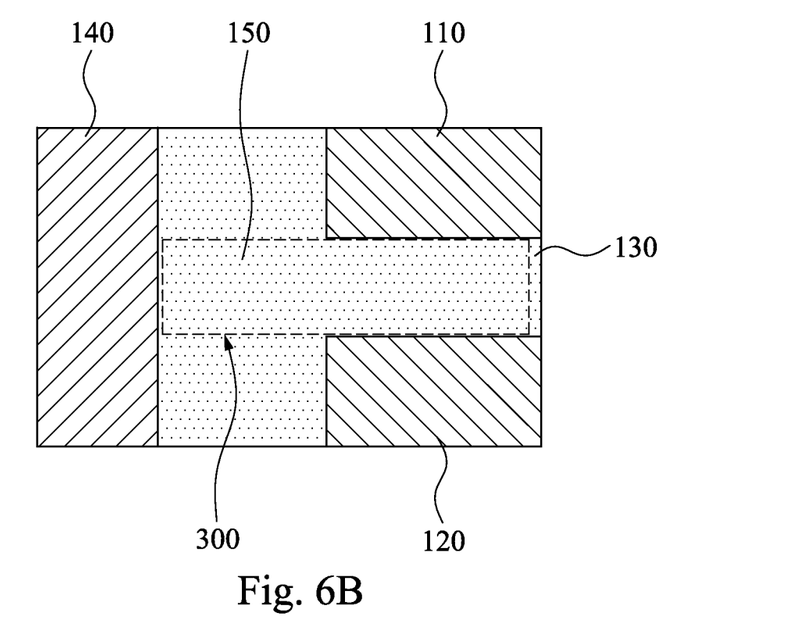
Figure 6C:
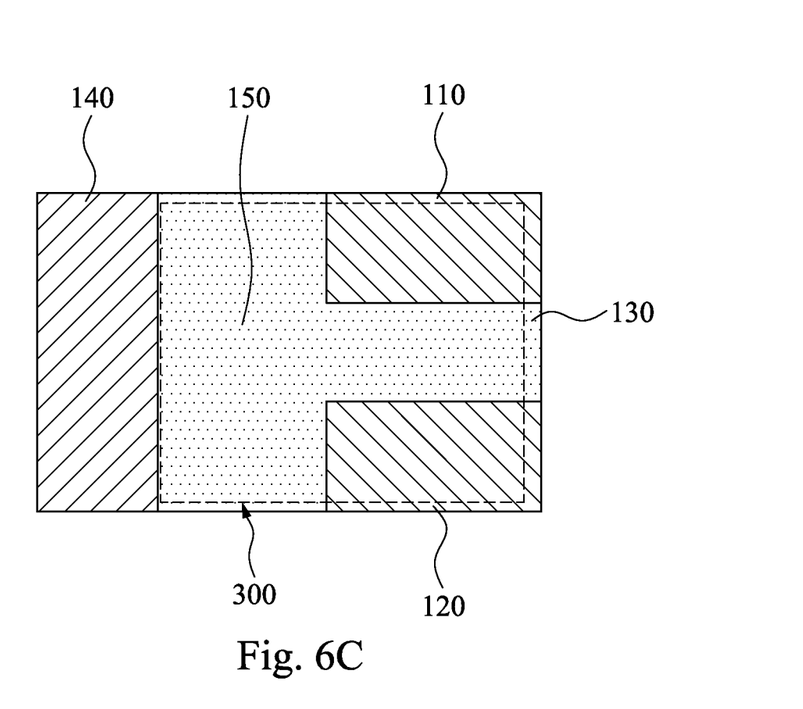

FIGS. 6A-6C are top views of substrates 100 and sensing wells 200 in accordance with some embodiments. In FIG. 6A, the sensing well 300 is disposed beneath (or adjacent to) the sensing region 130. The sensing well 300 exposes the sensing region 130. In FIG. 6B, the sensing well 300 is further disposed beneath (or adjacent to) the channel region 130. That is, the sensing well 300 is disposed beneath (or adjacent to) the sensing region 150 and the channel region 130. The sensing well 300 exposes the sensing region 150 and the channel region 130. In FIG. 6C, the sensing well 300 is further disposed beneath (or adjacent to) the source region 110 and the drain region 120. That is, the sensing well 300 is disposed beneath (or adjacent to) the sensing region 150, the channel region 130, the source region 110, and the drain region 120. The sensing well 300 exposes the sensing region 150, the channel region 130, the source region 110, and the drain region 120. In some other embodiments, the sensing well 300 is disposed beneath (or adjacent to) the sensing region 150, the channel region 130, the source region 110, and/or the drain region 120. Basically, embodiments fall within the claimed scope if the sensing well 300 is at least disposed adjacent to the sensing region 150.

Figure 7A:
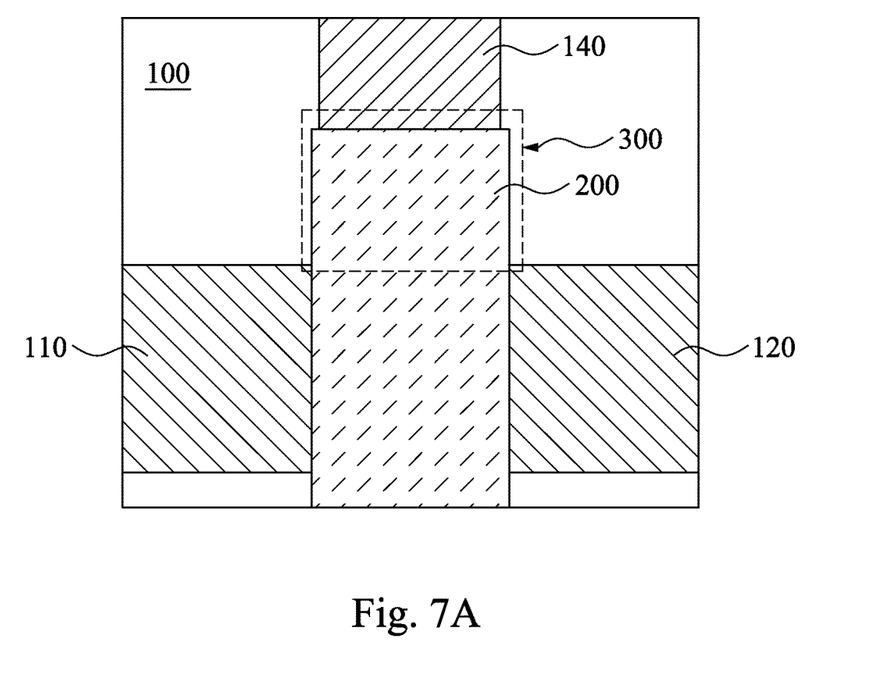
FIG. 7A is a top view of a biological device in accordance with some embodiments.
Figure 7B:
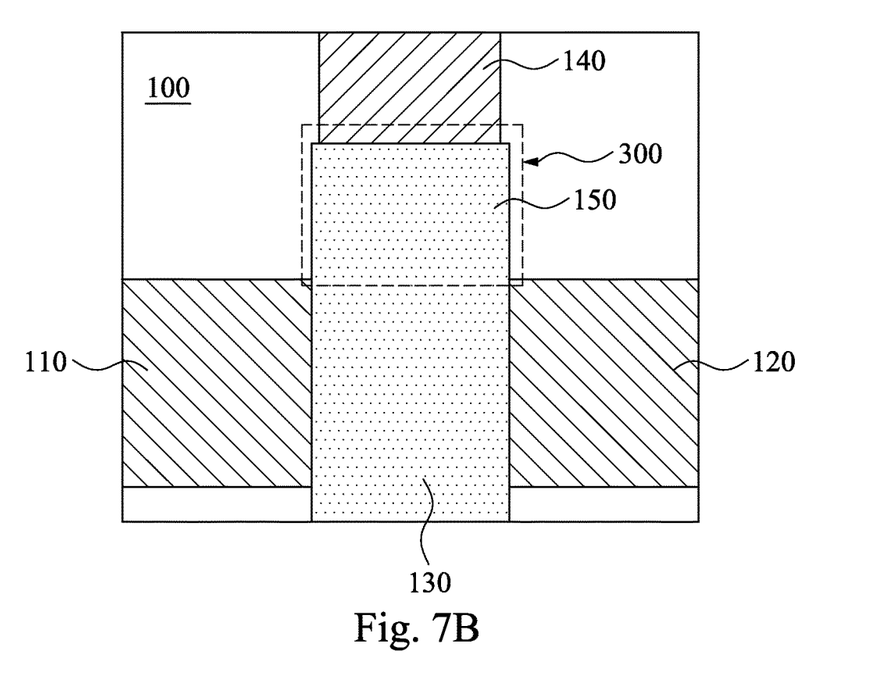
FIG. 7B is a top view of a substrate and a sensing well in FIG. 7A.

Reference is made again to FIGS. 1A and 1B. In FIGS. 1A and 1B, the sensing region 150 and the channel region 130 form a T-shaped figure. Accordingly, the gate electrode 200 is T-shaped. However, the shapes of the sensing region 150, the channel region 130, and the gate electrode 200 are not limited in this respect. FIG. 7A is a top view of a biological device in accordance with some embodiments, and FIG. 7B is a top view of a substrate 100 and a sensing well 300 in FIG. 7A. For clarity, the gate dielectric 170 (see FIG. 2) is omitted in FIG. 7A. In FIGS. 7A and 7B, the sensing region 150 and the channel region 130 form an I-shaped figure. Accordingly, the gate electrode 200 is I-shaped. The sensing well 300 is disposed beneath the sensing region 150. In some other embodiments, however, the sensing region 150 can extend to the channel region 130, even to the source region 110 and/or drain region 120.

Figure 8A:
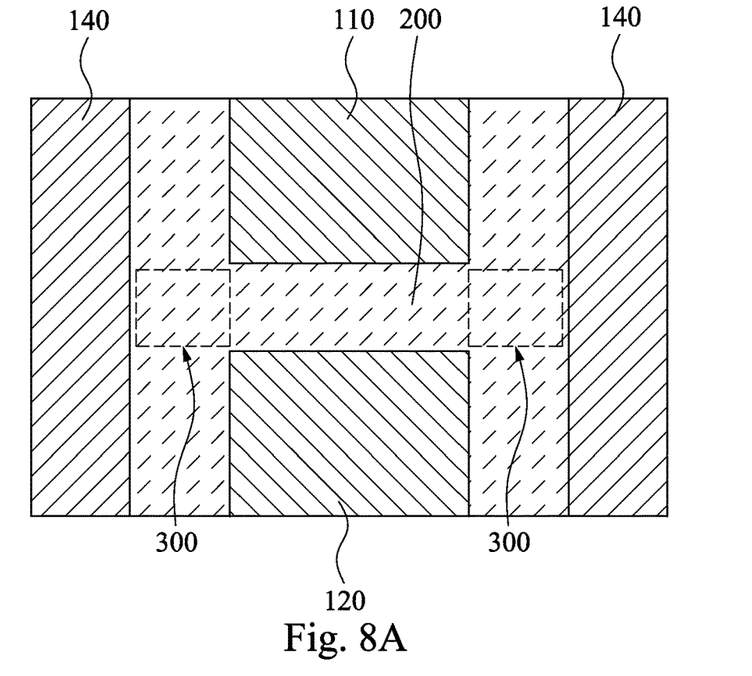
FIG. 8A is a top view of a biological device in accordance with some embodiments.
Figure 8B:
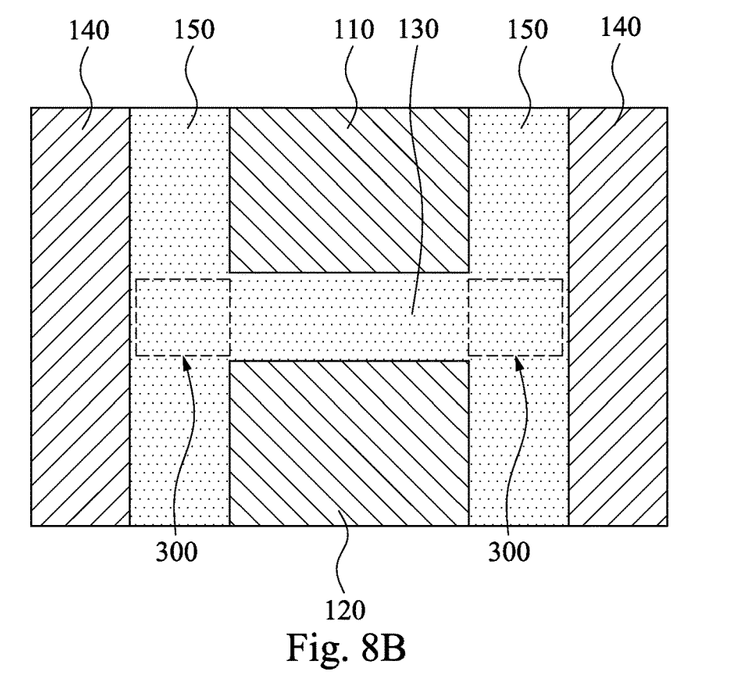
FIG. 8B is a top view of a substrate and a sensing well in FIG. 8A.

FIG. 8A is a top view of a biological device in accordance with some embodiments, and FIG. 8B is a top view of a substrate 100 and a sensing well 300 in FIG. 8A. For clarity, the gate dielectric 170 (see FIG. 2) is omitted in FIG. 8A. In FIGS. 8A and 8B, there are two sensing regions 150, two body regions 140, and two sensing wells 200. The channel region 130 is disposed between two of the sensing regions 150, and the two sensing regions 150 are respectively disposed between the two body regions 140 and the channel region 130. The two sensing regions 150 and the channel region 130 form an H-shaped figure. Accordingly, the gate electrode 200 is H-shaped. The sensing wells 200 are respectively disposed beneath the two sensing regions 150. In some other embodiments, however, the sensing regions 150 can respectively extend to the channel region 130, even to the source region 110 and/or drain region 120. Alternatively, the two sensing wells 200 can be combined.

Figure 9:
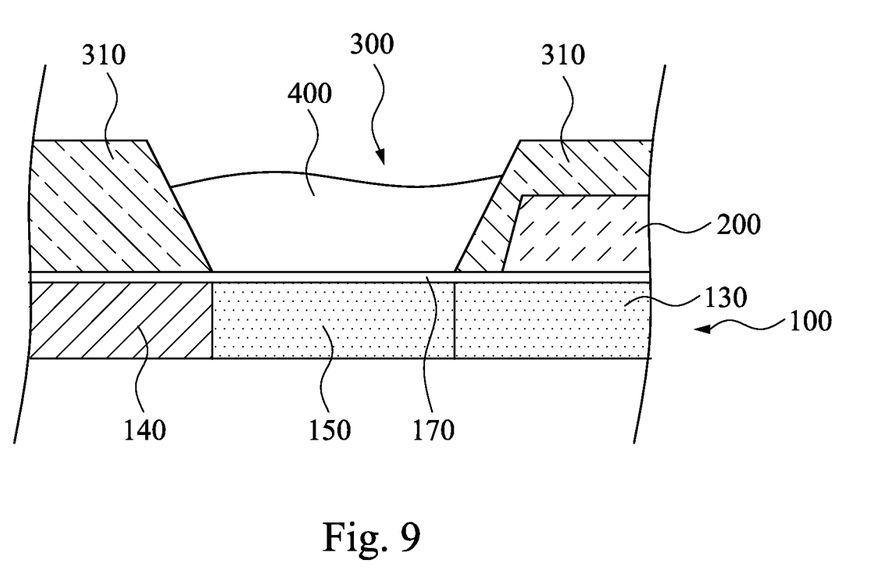
FIG. 9 is a cross-sectional view of a biological device in accordance with some embodiments.

FIG. 9 is a cross-sectional view of a biological device in accordance with some embodiments. The cross-sectional position of FIG. 9 is the same as the cross-sectional position of FIG. 2. In FIG. 9, both of the sensing well 300 and the gate electrode 200 are disposed on the substrate 100. The sensing well 300 is disposed on the sensing region 150, and the gate electrode is disposed on the channel region 130. Other relevant structural details of the biological device in FIG. 9 are similar to the biological device of FIG. 2, and, therefore, a description in this regard will not be repeated hereinafter.

It is understood that the embodiments of the biological device mentioned above are provided as examples and are not intended to be limited. The biological device may have different configurations consistent with the spirit of the present disclosure in alternative embodiments depending on real situations and manufacturing concerns.

In the aforementioned embodiments, a depletion region can be formed in the sensing region of the substrate. When the liquid analyte is disposed in the sensing well, the charging biomolecules therein can affect the depletion behavior of the depletion region, thereby affecting the threshold voltage of the transistor. Furthermore, the threshold voltage is changed according to the charging volume and the charge type of the charging biomolecules. Hence, by measuring the threshold voltage, the charging volume and the type of the charging biomolecules can be identified. Since the depletion behavior of the depletion region is sensitive to the charging performance of the liquid analyte, the sensitivity of the biological device can be improved. Furthermore, the source region, the drain region, and the channel region of the transistor can form a switch to control the on/off state of the biological device. In other words, the biological device does not connect to an additional switch, which occupies an additional area, resulting in a small device size. Hence, the density of the biological devices can be increased.

An aspect of the present disclosure is to provide a biological device including a substrate, a gate electrode, and a sensing well. The substrate includes a source region, a drain region, a channel region, a body region, and a sensing region. The channel region is disposed between the source region and the drain region. The sensing region is at least disposed between the channel region and the body region. The gate electrode is at least disposed on or above the channel region of the substrate. The sensing well is at least disposed adjacent to the sensing region.

Another aspect of the present disclosure is to provide a biological device including a substrate, a gate electrode, and a sensing well. The substrate includes a channel region, a source region, a drain region, a body region, and a sensing region. The source region and the drain region are respectively disposed at opposite sides of the channel region. The body region is separated from the channel region. The sensing region is physically connected the body region to the channel region. The gate electrode is at least disposed on or above the channel region. The channel region, the source region, the drain region, and the gate electrode form a transistor. The sensing well exposes the sensing region.

Still another aspect of the present disclosure is to provide a method for biosensing including providing a biological device. The biological device includes a substrate, a gate electrode, and a sensing well. The substrate includes a source region, a drain region, a channel region, a body region, and a sensing region. The channel region is disposed between the source region and the drain region. The sensing region is at least disposed between the channel region and the body region. The gate electrode is at least disposed on or above the channel region of the substrate. The sensing well is at least disposed adjacent to the sensing region. A depletion region is formed in the sensing region. A liquid analyte is disposed in the sensing well. A threshold voltage between the source region and the drain region is measured.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A device comprising:
   a substrate comprising:
     a source region and a drain region;
     a channel region disposed on a same plane as the source region and the drain region and between the source region and the drain region in a first lateral direction on the plane;
     a body region; and
     a sensing region disposed at least on the same plane as the channel region and between the channel region and the body region in a second lateral direction on the plane different from the first lateral direction, wherein the sensing region is configured to bind target molecules;
   a gate electrode disposed on the substrate;
   a sensing well disposed at least adjacent to the sensing region; and
   a gate dielectric disposed between the sensing region and the gate electrode.

2. The device of claim 1, further comprising:
   a bias source electrically connected to the body region.

3. The device of claim 2, wherein the bias source is a tunable bias source.

4. The device of claim 1, wherein the sensing well is disposed beneath the channel region.

5. The device of claim 1, wherein the sensing well is disposed beneath the source region and the drain region.

6. The device of claim 1, wherein the sensing region is disposed between the source region and the body region and between the drain region and the body region in the second lateral direction.

7. The device of claim 1, wherein the channel region is disposed between two sensing regions, and the two sensing regions are respectively disposed between two body regions and the channel region.

8. The device of claim 1, wherein the gate electrode is T-shaped, I-shaped, or H-shaped.

9. The device of claim 1, wherein the gate electrode is further disposed above the sensing region, and the sensing well is disposed beneath the sensing region.

10. The device of claim 1, wherein the sensing well is disposed above the sensing region.

11. The device of claim 1, wherein the sensing well exposes at least a portion of the sensing region and does not expose any portion of the channel region.

12. The device of claim 1, wherein the gate electrode is disposed directly on the gate dielectric.

13. A device comprising:
    a substrate comprising:
      a channel region;
      a source region and a drain region respectively disposed on a same plane as the channel region and at opposite sides of the channel region in a first lateral direction on the plane;
      a body region separated from the channel region; and
      a sensing region disposed on the same plane as the channel region and physically connecting the body region to the channel region in a second lateral direction on the plane different from the first lateral direction, wherein the sensing region is configured to bind target molecules;
    a gate electrode disposed on the substrate, wherein the channel region and the sensing region are on a same side of the gate electrode;
    a sensing well that exposes at least part of the sensing region; and
    a gate dielectric disposed between the gate electrode and the substrate, and above at least the body region, the sensing region and the channel region.

14. The device of claim 13, wherein at least part of the sensing region is a depletion region.

15. The device of claim 13, wherein the sensing well does not expose any portion of the channel region, and where the sensing well is on a first surface of the substrate and the gate electrode is on a second surface of the substrate, the second surface being opposite to the first surface.

16. The device of claim 13, wherein the gate electrode is disposed directly on the gate dielectric.

17. A method for biosensing comprising:
    providing a device, comprising:
      a substrate comprising:
        a source region and a drain region;
        a channel region disposed on a same plane as the source region and the drain region and between the source region and the drain region in a first lateral direction on the plane;
        a body region; and
        a sensing region at least disposed on the same plane as the channel region and between the channel region and the body region in a second lateral direction on the plane different from the first lateral direction, wherein the sensing region is configured to bind target molecules;
      a gate electrode disposed on the channel region and the sensing region of the substrate;
      a sensing well disposed at least adjacent to the sensing region; and
      a gate dielectric disposed between the gate electrode and the substrate, and above at least the sensing region and the channel region, wherein the gate dielectric extends as a layer from the sensing region to the channel region;
    forming a depletion region in the sensing region;
    disposing a liquid analyte in the sensing well; and
    measuring a threshold voltage between the source region and the drain region.

18. The method of claim 17, wherein forming the depletion region comprises applying a bias to the body region.

19. The method of claim 18, wherein the bias is a negative bias.

20. The method of claim 18, wherein the bias is a positive bias.

21. The method of claim 17, wherein forming the depletion region comprises performing a plasma treatment to the sensing region.

22. The method of claim 17, wherein forming the depletion region comprises performing an ion implantation process to the sensing region.

23. The method of claim 17, wherein the source region and the drain region are formed of N-doped materials, and the channel region, the body region, and the sensing region are formed of P-doped materials.

24. The method of claim 17, wherein the source region and the drain region are formed of P-doped materials, and the channel region, the body region, and the sensing region are formed of N-doped materials.

25. The method of claim 17, wherein the sensing well exposes at least a portion of the sensing region and does not expose any portion of the channel region.

26. The method of claim 17, wherein the gate electrode is disposed directly on a first side of the gate dielectric and the sensing region is disposed on a second side of the gate dielectric, the second side being opposite to the first side.

* * * * *